(12) United States Patent
Palumbo (10) Patent No.: US 9,323,035 B2
(45) Date of Patent: *Apr. 26, 2016

(54) ANNULAR OPTICAL DEVICE

(71) Applicant: Hach Company, Loveland, CO (US)

(72) Inventor: Perry A. Palumbo, Fort Collins, CO (US)

(73) Assignee: Hach Company, Loveland, CO (US)

(*) Notice: Subject to any disclaimer, the term of this patent is extended or adjusted under 35 U.S.C. 154(b) by 0 days.

This patent is subject to a terminal disclaimer.

(21) Appl. No.: 14/215,503

(22) Filed: Mar. 17, 2014

(65) Prior Publication Data

US 2015/0260970 A1    Sep. 17, 2015

Related U.S. Application Data

(63) Continuation of application No. 13/814,669, filed as application No. PCT/US2011/046105 on Aug. 1, 2011, now Pat. No. 8,675,198, application No. 13/814,669, which is a continuation-in-part of application No. 13/395,153, filed as application No. PCT/US2010/048091 on Sep. 8, 2010, now Pat. No. 8,687,286.

(60) Provisional application No. 61/371,381, filed on Aug. 6, 2010, provisional application No. 61/241,654, filed on Sep. 11, 2009.

(51) Int. Cl.
| | |
|---|---|
| *G02B 27/00* | (2006.01) |
| *G02B 19/00* | (2006.01) |
| *G02B 3/04* | (2006.01) |
| *G02B 3/00* | (2006.01) |

(52) U.S. Cl.
CPC .............. *G02B 19/0076* (2013.01); *G02B 3/04* (2013.01); *G02B 19/0028* (2013.01); *G02B 2003/0093* (2013.01)

(58) Field of Classification Search
CPC ........................................................ G02B 5/003
USPC ............................................................ 359/641
See application file for complete search history.

(56) References Cited

U.S. PATENT DOCUMENTS

| | | |
|---|---|---|
| 5,953,477 A | 9/1999 | Wach et al. |
| 8,724,107 B2 * | 5/2014 | Palumbo ...................... 356/338 |

* cited by examiner

*Primary Examiner* — James Jones
(74) *Attorney, Agent, or Firm* — Ference & Associates LLC (57) ABSTRACT

One embodiment provides an annular optical device, comprising: an annular meso-optic having a substantially triangular cross section and including an annulus centered about an axis of revolution; and a secondary optical structure substantially coaxial within the annulus of the annular meso-optic, wherein the secondary optical structure and the annular meso-optic are separated by a media comprising a media refractive index that is lower than a secondary optical structure refractive index, with the secondary optical structure being configured to hold a specimen to be radiated by impinging electromagnetic radiation directed into the secondary optical structure substantially along the axis of revolution, wherein re-directed radiation from the specimen is allowed into the annular meso-optic by the secondary optical structure if an angle of incidence of the re-directed radiation exceeds the angle of Total Internal Reflectance. Other embodiments are descried and claimed.

20 Claims, 6 Drawing Sheets

SECTION AA

SECTION AA

SECTION BB

FIG. 6

ANNULAR OPTICAL DEVICE

CROSS REFERENCE TO RELATED APPLICATIONS

This application is a continuation of U.S. patent application Ser. No. 13/814,669 ("the '669 application") filed Feb. 6, 2013; the '669 application is a national phase application of PCT/US2011/46105 filed Aug. 1, 2011, which is a non provisional of U.S. Provisional Patent Application No. 61/371,381 filed Aug. 6, 2010, and the '669 application is also a continuation in part of U.S. application Ser. No. 13/395,153 filed Mar. 9, 2012, which is national phase application of international application PCT/US2010/048091 filed Sep. 8, 2010, which is a non provisional of U.S. Provisional Patent Application No. 61/241,654 filed Sep. 11, 2009; the contents of each referenced application are hereby incorporated by reference.

FIELD OF THE INVENTION

The present invention relates to an optical device, and more particularly, to an annular optical device.

BACKGROUND OF THE INVENTION

A difficulty is found in the measurement of weak electromagnetic radiation, such as optical radiation or electromagnetic radiation of wavelengths of about 0.01 to 1000 micrometers (um). Such weak radiation may comprise the light produced by the emission of a fluorescent or luminescent specimen or the reflectance signal of a particle in a suspension media as in the measure of a turbid specimen for the determination of concentration.

In such circumstances, a difficulty is in the discrimination between the inherent noise of a detection system and the signal value produced by the specimen. The Signal to Noise Ratio (SNR) is a measure of signal value relative to the noise value of a detection system. In practice, a signal value approximately twice the noise value is considered a practical limit of a detection system for discriminating with confidence the signal value from the noise value.

Various methods can be employed to reduce inherent noise value of a detection system, such as cooling of the detector to reduce the thermal generation of random electrons or by employing signal processing techniques such as signal averaging. But these methods are limited in application or effectiveness, wherein a limit is reached wherein little or no further reduction of the noise value can be achieved by signal processing.

If the noise value of the detector cannot be further reduced, then improvements to the SNR can only be achieved through increases in the signal value. One common method employed to improve the signal value is to concentrate the radiation onto the detector. Another method is to increase the intensity of the stimulating radiation. However, increasing the intensity of the stimulating beam may result in damage of the specimen due to heating or breaking of molecular bonds, and is therefore limited to some threshold of practicality.

Conventional optical elements for the concentration of optical radiation, such as lenses or mirrors, are directional in nature, collecting radiation emitted along a specific ray path from a specific direction or area of origin. Typically, systems utilized in the detection of weak optical signals are positioned substantially perpendicularly to the incident beam of stimulating radiation so as to maximize the SNR. Additionally, much of the radiation emitted by fluorescence or particle scatter goes undetected as consequence of a finite subtended angle of the radiation concentrator device.

Another source of noise which can affect the SNR of an optical measurement system is stray radiation. Stray radiation is detectable radiation which impinges upon the detection device, generating a signal unrelated to the specimen or electromagnetic phenomenon under examination. As an example, radiation which is received in the detector, but which did not propagate through or interact with the sample, is a common stray radiation.

SUMMARY OF THE INVENTION

One embodiment provides an annular optical device, comprising: an annular meso-optic having a substantially triangular cross section and including an annulus centered about an axis of revolution; and a secondary optical structure substantially coaxial within the annulus of the annular meso-optic, with the secondary optical structure being configured to hold a specimen to be radiated by impinging electromagnetic radiation directed into the secondary optical structure substantially along the axis of revolution, wherein the secondary optical structure and the annular meso-optic are separated by a media comprising a media refractive index that allows re-directed radiation from the specimen into the annular meso-optic if an angle of incidence of the re-directed radiation exceeds the angle of Total Internal Reflectance.

Another embodiment provides a method of forming an annular optical device, the method comprising: providing an annular meso-optic having a substantially triangular cross section and including an annulus centered about an axis of revolution; and providing a secondary optical structure substantially coaxial within the annulus of the annular meso-optic, with the secondary optical structure being configured to hold a specimen to be radiated by impinging electromagnetic radiation directed into the secondary optical structure substantially along the axis of revolution, wherein the secondary optical structure and the annular meso-optic are separated by a media comprising a media refractive index that allows re-directed radiation from the specimen into the annular meso-optic if an angle of incidence of the re-directed radiation exceeds the angle of Total Internal Reflectance.

The foregoing is a summary and thus may contain simplifications, generalizations, and omissions of detail; consequently, those skilled in the art will appreciate that the summary is illustrative only and is not intended to be in any way limiting.

For a better understanding of the embodiments, together with other and further features and advantages thereof, reference is made to the following description, taken in conjunction with the accompanying drawings. The scope of the invention will be pointed out in the appended claims.

BRIEF DESCRIPTION OF THE DRAWINGS

The same reference number represents the same element on all drawings. The drawings are not necessarily to scale.

DETAILED DESCRIPTION OF THE INVENTION

FIGS. 1-6 and the following description depict specific examples to teach those skilled in the art how to make and use the best mode of the invention. For the purpose of teaching inventive principles, some conventional aspects have been simplified or omitted. Those skilled in the art will appreciate variations from these examples that fall within the scope of the invention. Those skilled in the art will appreciate that the features described below can be combined in various ways to form multiple variations of the invention. As a result, the invention is not limited to the specific examples described below, but only by the claims and their equivalents.

Figure 1:
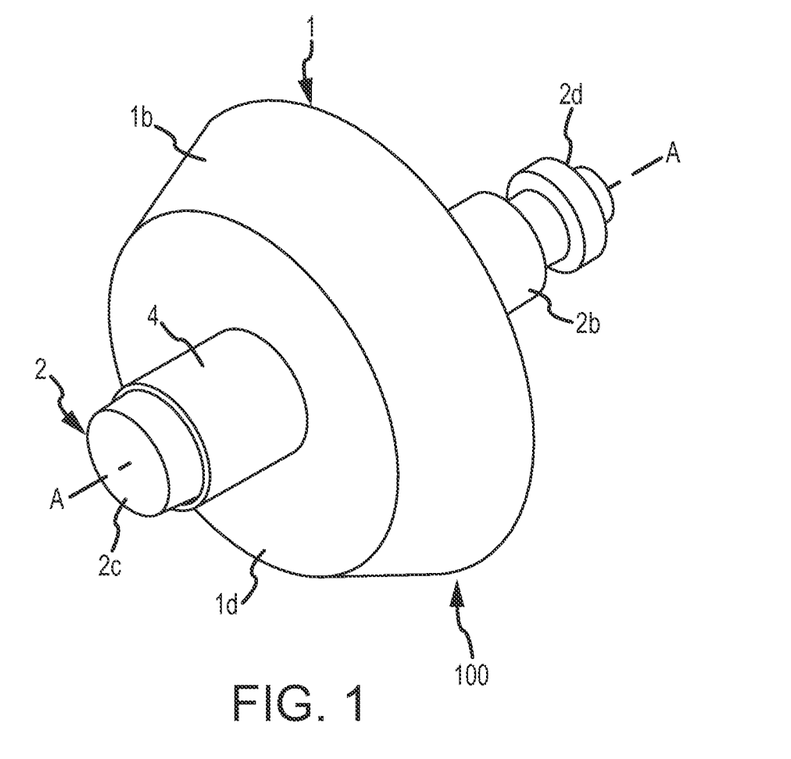
FIG. 1 is an isometric view of an annular optical device according to an embodiment of the invention.

FIG. 1 is an isometric view of an annular optical device 100 according to an embodiment of the invention. The annular optical device 100 comprises an annular meso-optic 1 and a secondary optical structure 2 that are substantially centered about an axis of revolution A. The annular meso-optic 1 includes an annulus 11 that passes through the annular meso-optic 1 and is also substantially centered on the axis of revolution A (see FIG. 4). The secondary optical structure 2 resides in the annulus 11 and as a result the secondary optical structure 2 is substantially coaxial to the annular meso-optic 1. The secondary optical structure 2 may be positioned within the annulus 11 so that the secondary optical structure 2 extends at least partially through the annular meso-optic 1 in some embodiments. The secondary optical structure 2 may be positioned to extend fully through the annulus 11 and the annular meso-optic 1 in some embodiments.

The annular optical device 100 can comprise a component of an optical instrument. The annular optical device 100 can comprise a component of any device that employs scattered, reflected, refracted, redirected, or transmitted light (or other visible or invisible electromagnetic radiation). As used herein, "re-directs" encompasses various mechanisms of light re-radiation including scattering, luminescing, refracting, etc.

The annular optical device 100 can comprise a component of any device that uses light to detect, measure, and/or characterize foreign matter, such as particulates, in a fluid. For example, the annular optical device 100 can comprise a component of a device used to detect and/or quantify particulates in water. However, the fluid can comprise any manner of gases or liquids and can comprise various combinations of gases, liquids, and/or solids. The annular optical device 100 can comprise a component of a turbidimeter or nephelometer in some embodiments.

The annular optical device 100 can receive light (or other radiation) directed along the axis of revolution A, into the secondary optical structure 2, wherein the annular optical device 100 captures only light that is substantially radially scattered within the secondary optical structure 2. The annular optical device 100 re-directs the scattered light back out, substantially parallel to the axis of revolution A and substantially opposite in direction to the impinging radiation. The annular optical device 100 therefore re-directs the radiation as a planar wave front. The annular meso-optic 1 of the embodiments herein comprises an axicon. Axicons are optical elements that are useful in converging optical radiation propagating as a planar wave front into a linear foci, or conversely, collimating a radially divergent linear segment of optical radiation to a planar wave front. Specifically, an annular axicon performs the convergence or collimation about an axis of revolution wherein the axicon does not occupy the space along the line of focus. Annular axicons are particularly useful wherein the line of focus or line of radial divergence is substantially perpendicular to the planar wave front.

The secondary optical structure 2 and the annular meso-optic 1 are separated by a media 12. Media 12 includes a media refractive index that is lower than a secondary optical structure refractive index.

The secondary optical structure 2 comprises a container including an open end 2a, a wall 2b, and a closed end 2c in some embodiments. In some embodiments, the secondary optical structure 2 includes a radiation-transmittable closed end 2c that is configured to substantially admit impinging electromagnetic radiation. In some embodiments, the secondary optical structure 2 includes at least one radiation-transmittable region in the wall 2b and about and/or along the line of focus 7 of the annular meso-optic 1, with the at least one radiation-transmittable region being configured to substantially pass impinging electromagnetic radiation. Alternatively, the entire secondary optical structure 2 can be substantially transmittable to radiation. The radiation can travel out of the secondary optical structure 2 through the open end 2a.

The secondary optical structure 2 can hold a specimen 3 to be tested, measured, or otherwise quantified. It should be understood that the specimen 3 may be statically held within the secondary optical structure 2 or may be circulated within or circulated through the secondary optical structure 2.

The secondary optical structure 2 is configured to hold a specimen to be radiated by impinging electromagnetic radiation directed into the secondary optical structure 2 substantially along the axis of revolution A. Radiation may be directed into the secondary optical structure 2, such as a beam of light 5, for example. The radiation may mainly pass through the specimen 3 held in the secondary optical structure 2. However, at least some of the radiation may be scattered. The radiation may be scattered by the specimen 3 (or scattered by components of or materials of interest within the specimen 3) as the radiation transits the secondary optical structure 2. The radiation may be scattered at different angles.

The specimen 3 can comprise a gas, a liquid, or mixtures of gas, liquid, and/or solids. The specimen 3 may include particles of gas, liquid, or solids that are desired to be detected and/or quantified. The specimen 3 can include suspended particles or various mixtures, suspensions, or immiscible materials.

Placement of the secondary optical structure 2 within the annulus of the annular axicon/meso-optic 1 creates an angular propagation limitation that controls the propagation of radiation into the annular optical device 100. Radiation that exceeds a condition for Total Internal Reflection (TIR) is allowed to pass through the secondary optical structure 2 and propagate into the annular axicon. This is shown by the ray 5f in FIG. 4. However, radiation that is reflected due to TIR propagates only within the secondary optical structure 2; i.e., radiation within the secondary optical structure 2 is only allowed to exit dependent upon the angle of incidence of the radiation to the optical surface of the secondary optical structure 2.

The secondary optical structure 2 is formed of a material such that radiation impinging on the walls of the secondary optical structure 2 at a relatively low angle will be internally reflected, refracted, or otherwise re-directed. This is illustrated by rays 5c and 5d of FIG. 4. If the angle of incidence is less than a predetermined incidence threshold, then the scattered radiation is internally re-directed by the secondary optical structure 2 and cannot pass into the annular meso-optic 1.

Figure 4:
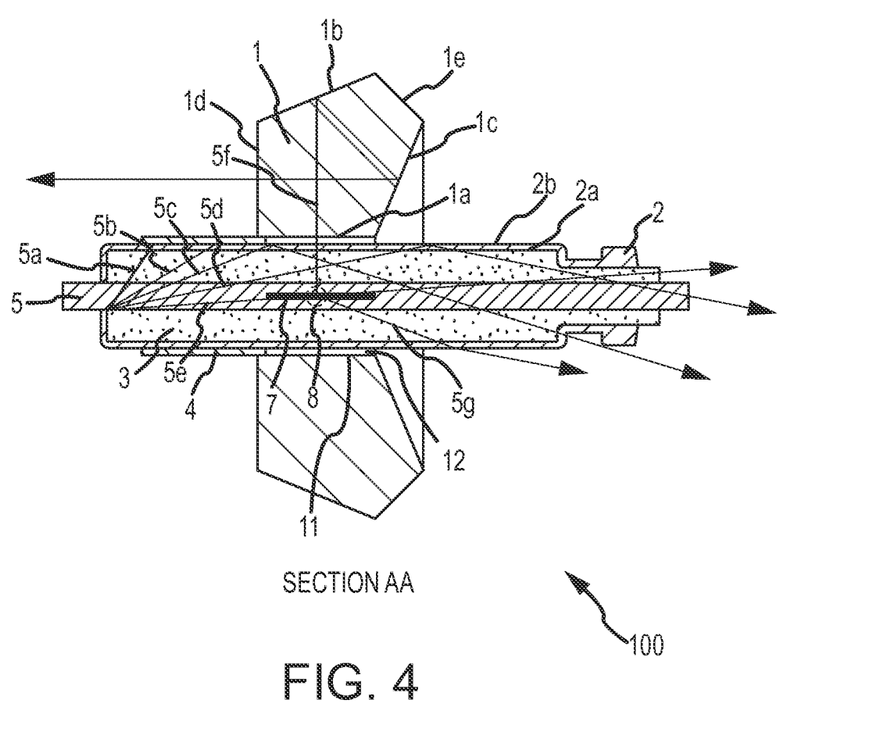
FIG. 4 is a section view AA of the annular optical device along the axis of revolution A.

The secondary optical structure 2 is positioned within the annulus 11 such that a line of focus 7 of the annular meso-optic 1 is located within the secondary optical structure 2, and therefore is located within the specimen 3 contained in the secondary optical structure 2. An optical beam 5 (or other beam of suitable electromagnetic radiation) may be projected along the axis of revolution A of the annular meso-optic 1, substantially along the line of focus 7. The measurement volume is defined by the chord length of the line of focus 7 and by the cross-sectional area of the optical beam 5. As a consequence, radiation scattered by the specimen 3 in the region of the line of focus 7 may leave the secondary optical structure 2 and enter the annular meso-optic 1 (see the ray 5*f*). The scattered radiation received in the annular meso-optic 1 is substantially radially divergent from a line of focus 7 of the annular meso-optic 1, regardless of an angular separation of the impinging electromagnetic radiation from the axis of revolution A. However, the secondary optical structure 2 restricts the scattered radiation and does not allow all scattered radiation to enter the annular meso-optic 1.

Scattered radiation from within the secondary optical structure 2 and within the annulus 11 of the annular meso-optic 1 is allowed into the annular meso-optic 1 by the secondary optical structure 2 if an angle of incidence of scattered radiation exceeds a predetermined incidence threshold. The annular meso-optic 1 re-directs the scattered radiation to comprise re-directed radiation that is substantially parallel to the axis of revolution A and substantially opposite in direction to the impinging electromagnetic radiation. The annular meso-optic may be preferentially positioned so as to re-direct the scattered radiation substantially parallel to the axis of revolution A and substantially in the same direction to the impinging electromagnetic radiation.

Therefore, scattered radiation that impinges on the wall of the secondary optical structure 2 at a relatively high angle, i.e., substantially radially, will not be internally re-directed and will exit the secondary optical structure 2. Consequently, the scattered radiation must be scattered substantially radially and substantially perpendicularly, i.e., at a high angle from the direction of the impinging electromagnetic radiation. Further, if the scattered radiation is within the annulus 11 of the annular meso-optic 1, then the scattered radiation will be re-directed by the annular meso-optic 1. In some embodiments, the scattered radiation must be scattered from within a span denoted by the line of focus 7. The re-directed radiation exits from the planar annular optical surface 1*d* of the annular meso-optic 1. As a result, the re-directed radiation will be directed substantially parallel to the axis of revolution A. The re-directed radiation may be substantially opposite in direction to the original, entering radiation. The re-directed radiation may comprise a substantially planar wave front.

Radially scattered radiation outside of either the annulus 11 or the line of focus 7 will not enter the annular meso-optic 1. Radially scattered radiation outside of either the annulus 11 or the line of focus 7 will not be re-directed by the annular meso-optic 1. If the angle of incidence of the scattered radiation is less than the predetermined incidence threshold, then the scattered radiation is internally re-directed by the secondary optical structure 2 and cannot pass into the annular meso-optic.

Similarly, even if the angle of incidence of the scattered radiation exceeds the predetermined incidence threshold, but the scattered radiation is scattered by the specimen in the region before the annular meso-optic 1, such as a region within the radiation-blocking structure 4, then the scattered radiation may still be prevented from leaving the secondary optical structure 2. Ray 5*g* propagates beyond the annular optical arrangement through secondary optical structure 2 and does not contribute to the measurable optical signal of interest. Ray 5*g* does not generate optical noise and ray 5*g* is considered to be loss.

The annular optical device 100 can further include a radiation-blocking structure 4 positioned over or incorporated into at least a portion of the secondary optical structure 2, as shown, wherein the radiation-blocking structure 4 blocks radiation scattered before encountering the annular meso-optic 1 and therefore prevents such scattered radiation from leaving the secondary optical structure 2. The radiation-blocking structure 4 can be formed of any appropriate radiation-absorbing material. The radiation-blocking structure 4 can be formed of any appropriate radiation-reflecting material. The radiation-blocking structure 4 can be formed of any appropriate radiation-impenetrable material.

The radiation-blocking structure 4 can be formed so as to fit over at least a portion of the secondary optical structure 2, as shown. The radiation-blocking structure 4 in some embodiments can extend at least partially out from the planar annular optical surface 1*d* of the annular meso-optic 1. As a result, radiation that is scattered substantially radially, but before the annulus 11, is blocked from leaving the secondary optical structure 2. As a result, this scattered radiation is therefore blocked from entering the planar annular optical surface 1*d* of the annular meso-optic 1. The radiation-blocking structure 4, comprising a radiation absorbing media, is located beyond the foci of the annular meso-optic 1.

In addition, the radiation-blocking structure 4 may provide a locating or positioning function. The radiation-blocking structure 4 may substantially center the secondary optical structure 2 within the annulus 11 of the annular meso-optic 1. The radiation-blocking structure 4 may create a desired size and uniformity of media 12 between the annular meso-optic 1 and the secondary optical structure 2.

Figure 2:
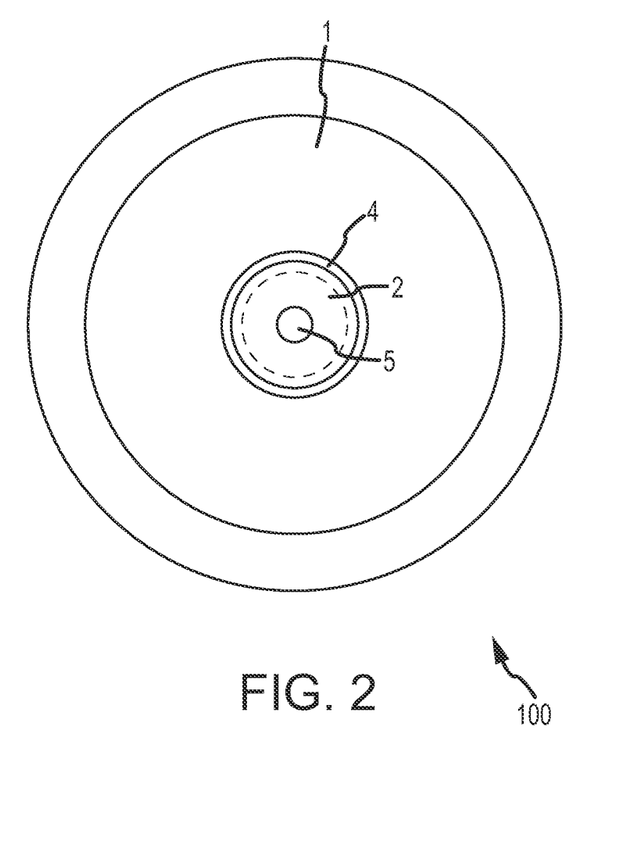
FIG. 2 is an end view of the annular optical device of FIG. 1.

FIG. 2 is an end view of the annular optical device 100 of FIG. 1. From this view, it can be seen that the annular meso-optic 1, the secondary optical structure 2, and the radiation-blocking structure 4 may be substantially coaxial. In some embodiments, the radiation-blocking structure 4 positions the secondary optical structure 2 substantially coaxially within the annulus 11 of the annular meso-optic 1. The radiation-blocking structure 4 prevents the outside surface of the secondary optical structure 2 from direct contact with the annular meso-optic 1 by centering the structure within the annulus of the annular meso-optic.

Figure 3:
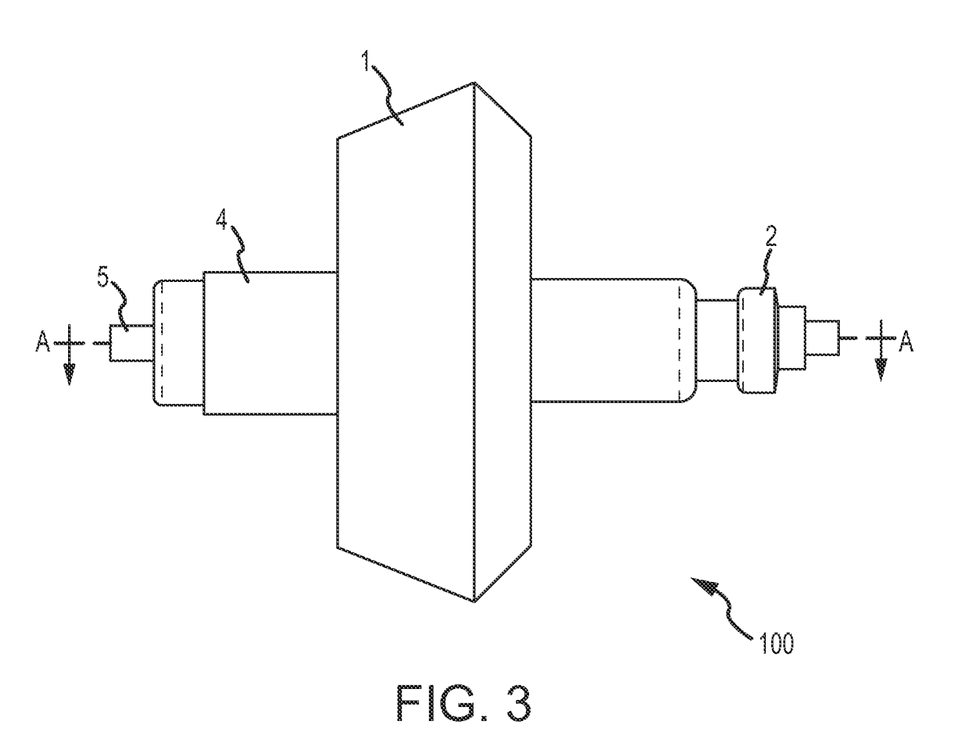
FIG. 3 is a side view of the annular optical device.

FIG. 3 is a side view of the annular optical device 100. In this figure, an optical beam 5 (or other radiation) is shown entering the closed end 2*c* of the secondary optical structure 2. In this embodiment, the secondary optical structure 2 extends from either side of the annular meso-optic 1, but it should be understood that the annular optical device 100 may be formed in other configurations and with other dimensions. The radiation-blocking structure 4 is located on the secondary optical structure 2 on the side before the annular meso-optic 1, i.e., between the source of the optical beam 5 and the annular meso-optic 1.

FIG. 4 is a section view AA of the annular optical device 100 along the axis of revolution A. The substantially hollow shape of the secondary optical structure 2 is shown in this section view. The solid shape of the annular meso-optic 1 and the annulus 11 therein are shown in this section view. The substantially pentagonal cross-sectional shape of the annular meso-optic 1 of this embodiment is shown in this section view.

It can be seen that media 12 exists between the annular meso-optic 1 and the secondary optical structure 2, specifically outside the wall 2*b* of the secondary optical structure 2.

Media 12 can comprise a media of air in some embodiments. Media 12, when comprised of air, will have a media refractive index that is lower than the refractive index of wall 2b of secondary optical structure 2 (i.e., the secondary optical structure refractive index). However, it should be understood that media 12 may be comprised of any suitable material that possesses an index of refraction lower than the wall 2b of the secondary optical structure 2. As a result of the lower index of refraction of media 12, a boundary exists between the wall 2b of the secondary optical structure 2 and the media 12 which will cause scattered radiation to be refracted, reflected, or otherwise internally re-directed by the secondary optical structure 2. If the scattered radiation has an angle of incidence less than a predetermined incidence threshold, then the scattered radiation will be re-directed and remain within the secondary optical structure 2. If the scattered radiation encounters the boundary with an angle of incidence greater than the predetermined incidence threshold, then the scattered radiation will not be re-directed and will exit the secondary optical structure 2 through wall 2b. Such high angle of incidence scattered radiation will be substantially radial in direction with respect to the secondary optical structure 2 and the annular meso-optic 1.

The secondary optical structure 2 can be formed of a suitable material or materials. The secondary optical structure 2 may be entirely transmittable to impinging radiation or may include windows or regions that are transmittable or semi-transmittable to radiation within an otherwise radiation-absorbing structure. The secondary optical structure 2 may include at least one radiation-transmittable region about the line of focus 7 of the annular meso-optic 1. The secondary optical structure 2 may include a radiation-transmittable closed end 2c that is configured to admit impinging electromagnetic radiation. Radiation-transmittable regions may be of different material, of different refractive index, or of different optical opacity. The secondary optical structure 2 is shown as comprising a substantially cylindrical container. However, the secondary optical structure 2 can be formed of other shapes, as desired.

The annular meso-optic 1 and the secondary optical structure 2 may comprise a portion of an instrument that quantifies particles in a specimen 3 by quantifying the scattering of impinging radiation. In some embodiments, the impinging radiation comprises visible or non-visible light. However, electromagnetic radiation of other wavelengths may also be employed.

The annular optical arrangement 100 provides utility in converging radiation from a substantially planar wave to a line of focus. Conversely, the annular optical arrangement 100 is capable of collimating a radially divergent linear segment of radiation to a substantially planar wave while advantageously restricting the amount of radiation not associated with the primary ray path of the optical arrangement from propagating out of the annular optical arrangement 100.

The annular meso-optic 1 of the embodiment shown comprises a solid annular meso-optic 1. The meso-optic is preferentially a solid of revolution about the axis of revolution A. The cross-sectional shape is preferably that of pentagon which forms a cylindrical optical surface 1a parallel to the axis of revolution and a planar annular optical surface 1d that is substantially perpendicular to the axis of revolution. An inner annulus of the planar annular optical surface 1d is coincident with the cylindrical optical surface 1a. Optical surfaces 1b and 1c are substantially conical with respect to the axis of revolution A and are convergent to a circular intersection at a distance radial to the axis of revolution. The conical optical surfaces 1b and 1c are preferentially coated to reflect radiation impingent upon the internal optical surfaces. In addition, the conical optical surface 1b is coincident to the outer annulus of the planar annular optical surface 1d and the conical optical surface 1c is coincident to the end of the cylindrical optical surface 1a opposite the planar annular optical surface 1d. Non-optical conical surface 1e terminates the convergence of conical optical surfaces 1b and 1c at a chord length along the axis of revolution not less than the length of the cylindrical optical surface 1a so as to reduce the cost of fabrication and fragility of the meso-optic element without vignette of the annular optical arrangement. The non-optical conical surface 1e is preferentially inclined about 45 degrees to the axis of revolution. The conical optical surfaces 1b and 1c are inclined relative to the axis of revolution so as to reflect or redirect radiation that is substantially perpendicularly radially divergent from the line of focus 7 to be substantially parallel to the line of focus 7. Conversely, the annular meso-optic 1 can redirect radiation that is traveling substantially parallel to the line of focus 7 to be substantially radially impinging on the line of focus 7 in the region of the cylindrical optical surface 1a.

An annular meso-optic as described possessing pentagonal cross-sectional annular volume of revolution converges planar waves of electromagnetic radiation to line of focus 7 substantially perpendicular to planar wave propagation or collimates optical radiation emitted radially divergent from line of focus 7 substantially perpendicular from the radial emission regardless of modest error in alignment of the annular pentagonal meso-optic axis of revolution to line of focus 7; such as a modest error in alignment of several degrees, for example.

It should be noted that annular meso-optic 1 need not be solid construction nor of pentagonal cross-sectional shape. Indeed, other conic surface(s) comprised of first-surface reflecting, refracting or diffractive surfaces can be used in the construction of an annular meso-optic in which the line of focus 7 is substantially coincident to the axis of revolution of the meso-optic.

In addition to the shown components and structures, any manner of additional lenses, components, and/or surfaces may be included in order to direct, collimate, disperse, condense, focus, magnify, and/or de-magnify the radiation. Additional components may be located before or after the annular optical device 100. For example, the annular optical device 100 may include a light or radiation source adjacent to and configured to direct radiation into the secondary optical structure 2. Further, a radiation detector may be positioned adjacent to the planar annular optical surface 1d of the annular meso-optic 1 in order to receive and quantify the radiation re-directed by the annular meso-optic 1 and exiting from the planar annular optical surface 1d.

It is obvious to those skilled in the art of optics, physics or electromagnetic theory that planar or spherical propagating waves of optical radiation may be manipulated by absorptive, refractive, diffractive and reflective elements alone or by incorporation with the annular optical device in order to collimate, magnify, de-magnify, disperse, condense, or bring to focus said radiation.

The solid annular meso-optic substrate material of the preferred embodiment may be that of any material transmittable to the radiation of interest. For example, in the visible electromagnetic spectrum, the impinging radiation may comprise electromagnetic radiation between approximately 380 nanometer (nm) to 780 nm, i.e., visible light as defined by the Commission internationale de l'eclairage (CIE). The substrate material may be that of Schott Glass N-BAK4, N-BK7, PMMA, or any other optically transmittable material. Further, the reflective coating on the conical optical surfaces 1b and 1c may be that of gold, silver, aluminum, or any other material reflective in the visible spectrum. In addition, the non-optical conical surface 1e may be coated with a light absorptive material such as black paint. The optical surfaces 1a and 1d may be uncoated or may be coated to reduce reflection loss at the wavelength(s) of interest. For applications in the visible wavelength range, an anti-reflective coating(s) may be that of an about quarter-wavelength thickness of magnesium fluoride (MgF2) applied to the transmittable optical surfaces 1a and 1d.

In one example, given an optical beam 5 of wavelength 0.5875618 micrometer (um) (i.e., the Fraunhofer 'd' helium emission wavelength) propagating in a surrounding media, like that of air, of refractive index 1.0000 along the line of focus 7 in a direction so as to enter the planar surface of the glass vial of refractive index 1.5168 into a specimen of refractive index 1.3330 into outside surfaces 2b of the vial also residing in the surrounding media. By Snell's Law of refraction, any redirection of optical beam 5 due to scatter or other optical phenomenon results in TIR if the angle of incidence to the inside wall 2a of the vial is greater than or equal to about 48.6 degrees, as measured from the normal or perpendicular to the axis of revolution of the cylindrical surface, as in rays 5c and 5d.

Figure 5:
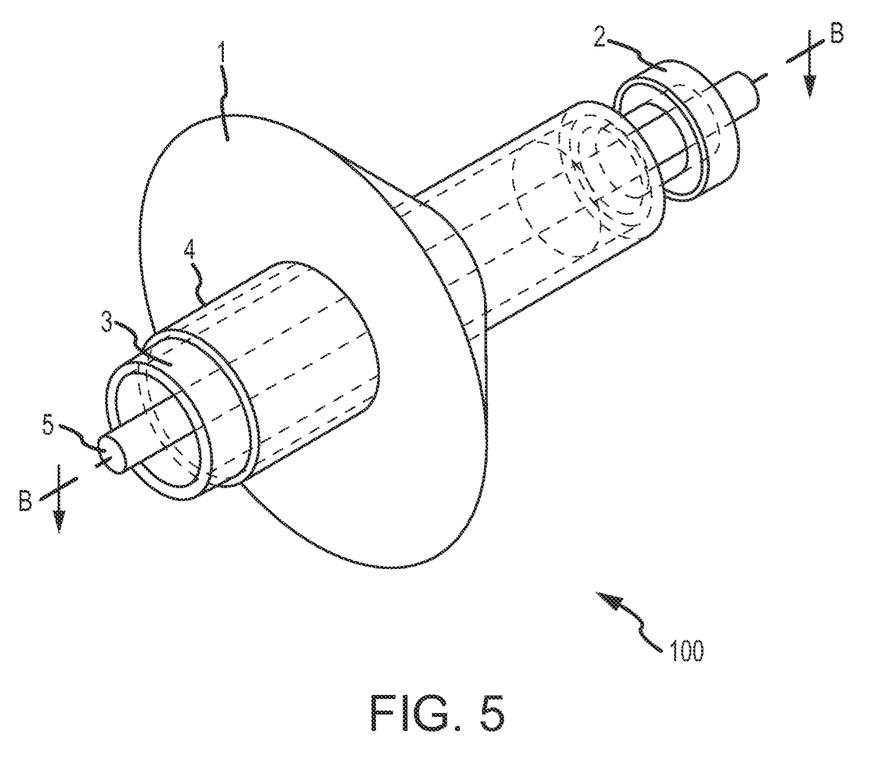
FIG. 5 shows the annular optical device according to another embodiment of the invention.

FIG. 5 shows the annular optical device 100 according to another embodiment of the invention. In this embodiment, the annular meso-optic 9 comprises a substantially triangular cross section of rotation, specifically a solid-of-revolution of a right angle triangle is shown. The triangular annular meso-optic 9 of this embodiment advantageously has one less optical surface to fabricate, features a shorter ray path, and requires less material. Along the axis of revolution of the annulus of the annular meso-optic 9 is the secondary optical structure 2. The secondary optical structure 2 and specimen 3 are coaxial to the triangular annular meso-optic 9. The previous discussion of the propagation of the radiation beam 5 and the rays 5a, 5b, 5c, 5d, 5e, 5f and 5g is likewise applicable to this embodiment.

Figure 6:
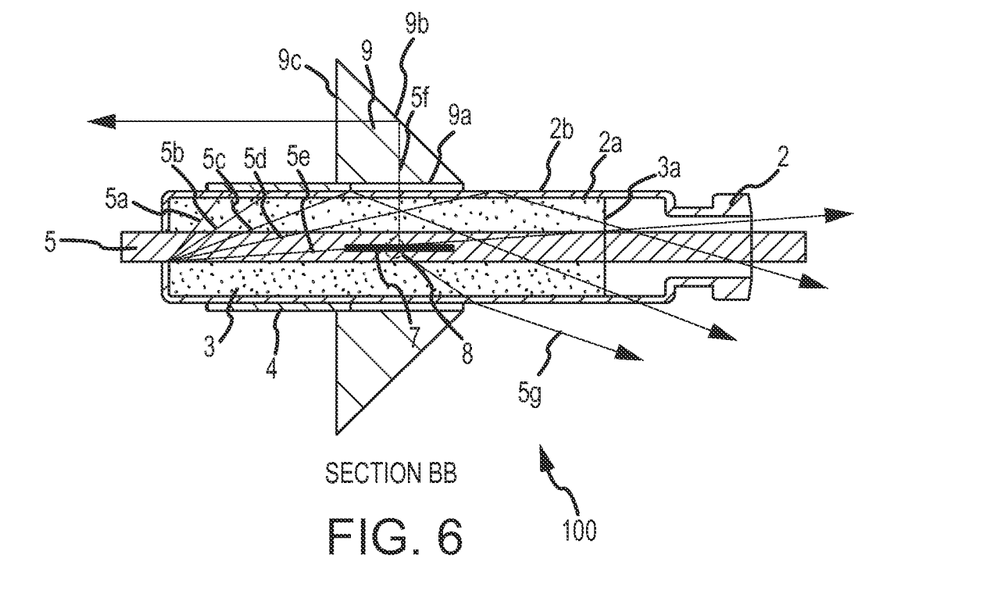
FIG. 6 is a section view BB of the annular optical device of FIG. 5.

FIG. 6 is a cross-section view BB of the annular optical device 100 of FIG. 5. In the figure, a conical optical surface 9b of the triangular annular meso-optic 9 is inclined relative to the axis of revolution A so as to reflect any radiation that is substantially perpendicularly radially divergent from the line of focus 7. The conical optical surface 9b redirects the radiation in a direction substantially parallel to the line of focus 7. The inner annulus of a planar annular optical surface 9c and a cylindrical optical surface 9a are coincident at one end of the cylindrical optical surface 9a. The conical optical surface 9b is coincident to an outer annulus of the planar annular optical surface 9c and is coincident to the cylindrical optical surface 9a at the end of cylindrical optical surface 9a that is opposite to the planar annular optical surface 9c. As in other embodiments, the conical optical surface 9b may be coated to reflect impinging radiation. The optical surfaces 9a and 9c may be discretionarily uncoated to reduce cost or coated to reduce reflection loss at the wavelength(s) of interest.

The disclosed annular optical device is not limited to the examples presented herein. Annular meso-optics comprising one or more conical optical surfaces may be used. Annular meso-optics with internally reflecting surface(s) or externally reflecting surface(s) may be used. It is further understood that the annular optical device may be formed by approximation of the conic optical surfaces using multiple radially segmented planar surfaces. In addition, variation in the cross-sectional curvature(s) of the surfaces of revolution may also be practiced by modification of one or more of the disclosed optical surfaces to optical surfaces that are substantially spherical, ellipsoidal, parabolic, or hyperbolic.

The annular optical device 100 may find use in the fields of, for example, fluorometry, flow cytometry, illuminators, laser optics, electromagnetic concentrators, flow metrology, nephelometry, and particle analysis. However, this listing is not exhaustive. It should be understood that other uses are contemplated and are within the scope of the description and claims.

The detailed descriptions of the above embodiments are not exhaustive descriptions of all embodiments contemplated by the inventors to be within the scope of the invention. Indeed, persons skilled in the art will recognize that certain elements of the above-described embodiments may variously be combined or eliminated to create further embodiments, and such further embodiments fall within the scope and teachings of the invention. It will also be apparent to those of ordinary skill in the art that the above-described embodiments may be combined in whole or in part to create additional embodiments within the scope and teachings of the invention. Accordingly, the scope of the invention should be determined from the following claims.

What is claimed is:

1. An annular optical device, comprising:
   a. an annular meso-optic having a substantially triangular cross section and including an annulus centered about an axis of revolution; and
   b. a secondary optical structure substantially coaxial within the annulus of the annular meso-optic, with the secondary optical structure being configured to hold a specimen to be radiated by impinging electromagnetic radiation directed into the secondary optical structure substantially along the axis of revolution, wherein the secondary optical structure and the annular meso-optic are separated by a media comprising a media refractive index that allows re-directed radiation from the specimen into the annular meso-optic if an angle of incidence of the re-directed radiation exceeds the angle of Total Internal Reflectance.

2. The annular optical device of claim 1 wherein after re-directed radiation is allowed into the annular meso-optic it reflects the radiation so that it is substantially parallel to the axis of revolution.

3. The annular optical device of claim 1 wherein the re-directed radiation is selected from the group consisting of the scatter, luminescence, reflectance and refraction of radiation, and wherein the media refractive index is lower than the refractive index of the secondary optical structure.

4. The annular optical device of claim 1, wherein the re-directed radiation received in the annular meso-optic is substantially radially divergent from a line of focus of the annular meso-optic, regardless of an angular separation of the impinging electromagnetic radiation from the axis of revolution.

5. The annular optical device of claim 1, wherein the re-directed radiation is received by the annular meso-optic and reflected substantially along the axis of revolution, wherein reflected radiation exits from a planar annular optical surface of the annular meso-optic.

6. The annular optical device of claim 1, wherein if the angle of incidence is less than the angle of Total Internal Reflectance, then the re-directed radiation is internally reflected by the secondary optical structure and cannot pass into the annular meso-optic.

7. The annular optical device of claim 1, with the secondary optical structure including a radiation-transmittable closed end that is configured to admit the impinging electromagnetic radiation.

8. The annular optical device of claim 1, with the secondary optical structure including at least one radiation-transmittable region about the line of focus of the annular meso-optic.

9. The annular optical device of claim 1, further comprising a radiation-blocking structure positioned over or incorporated into at least a portion of the secondary optical structure, wherein the radiation-blocking structure prevents radiation from leaving the secondary optical structure.

10. The annular optical device of claim 1, further comprising a radiation-blocking structure positioned over or incorporated into at least a portion of the secondary optical structure and extending at least partially out from a planar annular optical surface of the annular meso-optic.

11. The annular optical device of claim 1, further comprising a radiation-blocking structure positioned over or incorporated into at least a portion of the secondary optical structure and substantially centering the secondary optical structure within the annulus of the annular meso-optic.

12. A method of forming an annular optical device, the method comprising:
   a. providing an annular meso-optic having a substantially triangular cross section and including an annulus centered about an axis of revolution; and
   b. providing a secondary optical structure substantially coaxial within the annulus of the annular meso-optic, with the secondary optical structure being configured to hold a specimen to be radiated by impinging electromagnetic radiation directed into the secondary optical structure substantially along the axis of revolution, wherein the secondary optical structure and the annular meso-optic are separated by a media comprising a media refractive index that allows re-directed radiation from the specimen into the annular meso-optic if an angle of incidence of the re-directed radiation exceeds the angle of Total Internal Reflectance.

13. The method of claim 12 wherein after re-directed radiation is allowed into the annular meso-optic it reflects the radiation so that it is substantially parallel to the axis of revolution.

14. The method of claim 12 wherein the re-directed radiation is selected from the group consisting of the scatter, luminescence, reflectance and refraction of radiation, and wherein the media refractive index is lower than the refractive index of the secondary optical structure.

15. The method of claim 12, wherein the re-directed radiation received in the annular meso-optic is substantially radially divergent from a line of focus of the annular meso-optic, regardless of an angular separation of the impinging electromagnetic radiation from the axis of revolution.

16. The method of claim 12, wherein the re-directed radiation is received by the annular meso-optic and reflected substantially along the axis of revolution, wherein re-directed radiation exits from a planar annular optical surface of the annular meso-optic.

17. The method of claim 12, wherein if the angle of incidence is less than the angle of Total Internal Reflectance, then the re-directed radiation is internally reflected by the secondary optical structure and cannot pass into the annular meso-optic.

18. The method of claim 12, with the secondary optical structure including a radiation-transmittable closed end that is configured to admit the impinging electromagnetic radiation.

19. The method of claim 12, with the secondary optical structure including at least one radiation-transmittable region about the line of focus of the annular meso-optic.

20. The method of claim 12, further comprising providing a radiation-absorbing structure positioned over or incorporated into at least a portion of the secondary optical structure, wherein the radiation-blocking structure prevents radiation from leaving the secondary optical structure.

* * * * *